United States Patent [19]
Goldsmith

[11] Patent Number: 6,058,939
[45] Date of Patent: *May 9, 2000

[54] METHOD OF CONTROLLING THE SLEEP PATTERN OF AN INFANT

[76] Inventor: Derek John Goldsmith, Orchard House, Crockham Hill, Edenbridge, Kent TN8 6TE, United Kingdom

[ * ] Notice: This patent is subject to a terminal disclaimer.

[21] Appl. No.: 09/115,127

[22] Filed: Jul. 14, 1998

Related U.S. Application Data

[63] Continuation of application No. 08/748,590, Nov. 13, 1996, Pat. No. 5,778,892.

[51] Int. Cl.[7] .................................................. A61B 19/00
[52] U.S. Cl. ............................................. 128/898; 600/26
[58] Field of Search ...................................... 128/898, 897; 600/26–28, 558

[56] References Cited

U.S. PATENT DOCUMENTS 5,507,716  4/1996  LaBerge et al. .
5,778,892  7/1998  Goldsmith ............................... 128/898

OTHER PUBLICATIONS

Anders "Home–Recorded Sleep in 2– And 9–Month–Old Infants". J AM Acan Child Psychiatr 17(3): 421–32. (Jun. 1978).

Coons et al. "Development Of Sleep–Wake Patterns And Non–Rapid Eye Movement Sleep Stages During The First Six Months Of Life In Normal Infants". Pediatrics 69(6): 793–8 (Jun. 1982).

Benington et al. "Does The Function Of REM Sleep Concern Non–REM Sleep Or Waking?" Prog Neurobiol 44(5): 433–49 (1994).

Gaultier "Cordiorespiratory Adaptation During Sleep In Infants and Children". Pediatr Pulmonol 19(2): 105–17 (Feb. 1995).

Wolfson "Sleeping Patterns Of Children And Adolescents". Child ADN Adolescent Psychiatr Clinics of N AM 5(3): 549–568 (Jul. 1996).

*Primary Examiner*—Michael J. Milano
*Assistant Examiner*—Kelly O'Hara
*Attorney, Agent, or Firm*—Harness, Dickey & Pierce, P.L.C.

[57] ABSTRACT

A method of controlling the Sleep pattern of a baby by monitoring its state of sleep to ensure that it enters rapid eye movement sleep to ensure proper development of its central nervous system. If the baby does not enter the rapid eye movement sleep phase, then the baby may be frozen and is reawakened and comforted with smiles and laughter before being returned to sleep.

10 Claims, No Drawings

METHOD OF CONTROLLING THE SLEEP PATTERN OF AN INFANT

This is a continuation of U.S. patent application, Ser. No. 08/748,590 filed Nov. 13, 1996, now issued as U.S. Pat. No. 5,778,892.

BACKGROUND OF THE INVENTION

The present invention relates to a method of controlling the Sleep pattern of an infant to ensure proper psychological development.

Traditionally when a baby is put to sleep, it is assumed, as long as it is sleeping soundly, that it is receiving the full benefit of sleep. There is therefore no apparent advantage or reason to rewaken the baby, However, under certain circumstances, a baby may give the appearance of sleeping soundly when in fact it has not entered the important rapid eye movement (referred to herein as REM) phase of sleep.

This phenomenon results from an ancient mechanism designed to protect humans from losing their babies to predators. The mechanism allows mothers to "freeze" their infants, enabling them to be hidden to avoid threats such as predators, fires, storms, earthquakes, wars, etc. Once the danger has passed, the infant can be "unfrozen" and returned to a normal state by providing it with "danger over" signals. These comprise laughter, smiles, cuddles, suckling, stroking, rocking etc.

Although this mechanism is no longer required today, it is still active in about one quarter of the population. During the time that the infant is "frozen", proper development of the central nervous system is suspended. Prolonged periods of being in this frozen state, instead of proper REM sleep, prevent proper development of the infant. This affects about 1% of babies resulting in impairment of their central nervous system. This failure of the central nervous system to develop properly has enormous effects in terms of human suffering on the victims and their families. Furthermore, the financial cost to countries is enormous. For example, in the UK it is estimated to cost £1 billion annually.

The "frozen state" is a non-REM state in which orderly development of the central nervous system and processing therein are arrested. The frozen state is a pre-language state in which the infant baby is receptive and obedient to facial expression. This state developed in pre-language, post-ape man to compensate for the fact that babies were born helpless compared to apes, whose offspring would ride on their mothers back to escape from impending danger. In this state, the infant is silent and still, breathing is shallow, blood pressure changes and there in no explicit memory. However, most importantly in today's context, while it appears that the baby is sleeping properly there is no REM sleep. In this state, the baby is still receptive and in a state of increased strength which would allow the baby to be left clinging the branch of a tree or hidden/hung on a shelf in a cave or in a shelter or even floating, face up, in water.

The physical effects of entering the frozen state provide significant advantages in avoiding danger, particularly from predators. The baby is only responsive to its parents, so a predator is not going to be alerted to the presence of the baby by noise made by the baby. The baby has a reduced reaction to pain so the predator may take it for dead and leave it for later. Similarly, reduced blood pressure leads to reduced bleeding and again a predator may take the baby for dead. Furthermore, the baby's reduced reaction could allow it to be left in an apparently dangerous situation which again may deter a predator. For example, if there is a fire, the baby's reduced reaction could mean the predator is unwilling to risk negotiating a fire to investigate a still and silent baby, The lack of explicit memory will also protect the baby from post-trauma effects by having a memory of an unpleasant situation. The frozen state is entered when the baby detects fear or danger, particularly in its mother's face. The baby is unfrozen by laughter and happy smiling faces. It is well known that a new born baby can recognise and read its mother's or primary carer's face within a few days of birth. As a result of this, if the mother is in a state of fear or stress then this shows on her face and the baby reacts to this by entering the frozen state.

The frozen state is a partially instinctive and partially learned response and becomes more easily induced through repetition. In a modern context, language is used as a bonding/obedience control technique and as such the frozen state can be partly induced and/or resisted by the language process. As such, a baby can be susceptible to entering the frozen state as a result of the language it hears around it as well as the visual signals discussed above.

The living brain is a continuously developing structure and a considerable amount of organisation and processing is carried out during REM sleep which allows the brain to develop and process memories and learning acquired during the waking hours. Therefore, if the baby does not enter the RSM sleep state, this brain development does not occur properly and the baby is left underdeveloped. Failure of REM sleep to occur means that proper maturity of the central nervous system does not occur. It has been suggested that afflictions like schizophrenia, although they do not appear before late adolescence, are derived from factors which operate in the first months of life. Furthermore, schizophrenics show impairment and delay in acquisition of motor skills and language. Both symptoms of an underdeveloped central nervous system.

In a time when this mechanism was crucial for survival from predators, the mother would dictate when the baby was fed. This would usually be at a time when she felt relaxed and safe from danger herself. However, in the modern context it has become more appropriate for the mother to feed the baby on demand e.g. when it cries, such that the mother is dictated by the baby. This coupled with other environmental effects can lead to frustration in the mother causing her to become angry and/or anxious. This emotion is read by the baby in the mother's face. This coupled with aggressive language the baby may hear around it could cause it to enter the frozen state. This may appear to the mother that the baby is content and has fallen asleep, resulting in the mother laying the baby down and leaving it assuming it to be asleep. This results in the baby being left for extended periods in the frozen state in which development in the central nervous system is suspended.

SUMMARY OF THE INVENTION

According to the present invention, if an infant has not entered the rapid eye movement sleep within a predetermined period of time, then it is necessary to awaken the infant to provide it with comforting to relax it, so that it is no longer in the frozen state, before returning it to sleep. The present invention provides a method of controlling the sleep pattern of infants comprising checking the state of sleep of a sleeping infant and, if the infant has not entered rapid eye movement sleep, waking the infant; and comforting the infant until the infant returns to sleep.

Comforting of the infant may be provided by visual signals such as laughing or smiling, particularly when the infant can see its mother's (or primary carer's) face. Tactile or physical signals such as cuddling, suckling, stroking or rocking can also be used along with other signals such as auditory signals (talking, singing etc).

The state of sleep of an infant may be monitored by observing the movement of the infant's eyes beneath its eyelids by the mother or other person or by using apparatus to observe the eye movement or brain activity of the infant.

DETAILED DESCRIPTION OF THE PREFERRED MODE

The method of the present invention provides a means of monitoring the state of a baby when it is laid down to sleep. By checking to ensure that the baby has entered the REM sleep phase, the mother can ensure that the baby is not in the frozen state and in therefore sleeping correctly. Young babies enter REM sleep almost immadiately after falling asleep. Therefore, the mother can easily check the baby shortly after it goes to sleep. If after a short period it has not entered REM sleep, the mother can comfort the baby after gently awakening it, allowing the baby to see the mother's face and that she is no longer stressed or fearful. This causes the baby to come out of the frozen state and relax, such that when it laid down again and returns to sleep, it will go into REM sleep properly. As indicated above, various methods can be used to bring the baby out of the frozen state. These primarily include visual signals in the mother's face and physical contact and motion also coupled with soothing auditory and linguistic indications. It is believed that the learning of the freeze mechanism begins while the baby is still in the womb. Physical and/or chemical signals indicate to the baby that the mother is stressed and/or fearful and also when the danger has passed. These signals may still operate on the post-natal baby. Chemical messages indicative of safety to the baby cause it to relax and return to the normal state. These may be delivered to the baby through suckling its mother.

It has been found that a normal infant eventually learns to discriminate between fear and anger, but that this stage of development usually occurs only when the infant is from 12 to 18 months old. It is therefore felt that the method of the present invention can be helpful for an infant up to at least 18 months of age and it is contemplated that its use on an infant up to 2 years of age is desirable.

Although this new method of observation is easily carried out by the mother or other person, shortly after the baby goes to sleep, monitoring could be carried out by automatic monitoring means. This could be carried out by electronically monitoring the baby's lidded eyes to check for rapid motion of the eyeball beneath the eyelid. The apparatus could observe the baby's eyes after they have closed to check that this eye movement, indicative of REM sleep, occurs and if is does not occur within a period of time the apparatus can respond by sounding an alarm or providing some other warning to the baby minder. Alternatively, the baby's brain activity could be monitored to check that the REM phase of sleep has occurred within a specified period of time after the baby has gone to sleep.

Conmmercial devices (e.g. "Lucid Dreams" apparatus) already exist for monitoring sleep states and for flashing lights in a users eyes during REM sleep to enhance dreaming.

I claim:

1. A method for controlling the sleep pattern of an infant by causing such infant to enter rapid eye movement sleep, such method comprising:

(a) determining the state of sleep of the infant when sleeping and, responsive to a determination of non-rapid eye movement sleep:

(b) waking the infant;

(c) causing the infant to return to sleep; and (d) repeating steps (a) to (c) until the infant has entered rapid eye movement sleep.

2. A method according to claim 1 wherein, the step of causing the infant to sleep comprises at least one of visual, auditory and physical stimulation.

3. A method according to claim 2, wherein said stimulation is visual and involves showing to the infant a face of a primary carer in one of a laughing state and a smiling state.

4. A method according to claim 2, wherein said stimulation is auditory and is selected from the group consisting of the primary carer speaking to an infant using calming language and the primary carer making calming noises.

5. A method according to claim 2, wherein said stimulation is physical and is selected from the group consisting of suckling, stroking, cuddling, and gently moving and rocking the baby.

6. A method according to claim 1 wherein the step of determining the state of sleep of a sleeping infant comprises observing the lidded eyes of the sleeping infant to check for rapid motion of the eyeball beneath the eyelid.

7. A method according to claim 1 where the state of sleep of the infant is directly monitored by the primary carer.

8. A method according to claim 1 wherein the state of sleep is monitored by a monitoring device which provides an indication to a primary carer that the infant has not entered rapid eye movement sleep.

9. A method according to claim 1, wherein the infant has a mother and the mother is a primary carer.

10. A method according to claim 1, wherein the infant is no older than 18 months of age.

* * * * *

UNITED STATES PATENT AND TRADEMARK OFFICE
CERTIFICATE OF CORRECTION

PATENT NO. : 6,058,939
DATED : May 9, 2000
INVENTOR(S) : Derek John Goldsmith

It is certified that error appears in the above-identified patent and that said Letters Patent is hereby corrected as shown below:

On title page item [57],
Abstract line 1, "Sleep" should be --sleep--.

Column 1, line 10, "Sleep" should be --sleep--.

Column 2, line 27, "RSM" should be --REM--.

Column 3, line 17, "in" should be --is--

Column 3, line 18, "immadiately" should be --immediately--

Signed and Sealed this

Third Day of April, 2001

Attest:

NICHOLAS P. GODICI

*Attesting Officer*   *Acting Director of the United States Patent and Trademark Office*